(12) United States Patent
Che et al.

(10) Patent No.: US 8,168,138 B2
(45) Date of Patent: May 1, 2012

(54) CRYOGENIC VIAL

(76) Inventors: Li Che, Broadview Heights, OH (US); Zijiang Chen, Broadview Heights, OH (US)

( * ) Notice: Subject to any disclaimer, the term of this patent is extended or adjusted under 35 U.S.C. 154(b) by 13 days.

(21) Appl. No.: 12/975,763

(22) Filed: Dec. 22, 2010

(65) Prior Publication Data
US 2011/0143452 A1 Jun. 16, 2011

(51) Int. Cl.
*B01L 3/00* (2006.01)

(52) U.S. Cl. .......................... 422/501; 436/180

(58) Field of Classification Search .................. None
See application file for complete search history.

(56) References Cited

U.S. PATENT DOCUMENTS 5,325,980 A 7/1994 Grimm et al.
5,711,446 A 1/1998 Jeffs et al.

OTHER PUBLICATIONS

Hampton Research, retreived from internet: http://hamptonresearch.com/documents/product/0000000379-0000000765.pdf 2000.*

* cited by examiner

*Primary Examiner* — Yelena G Gakh
*Assistant Examiner* — Robert Xu
(74) *Attorney, Agent, or Firm* — Renner, Otto, Boisselle & Sklar, LLP

(57) ABSTRACT

Provided is a cryogenic vial for storing at least one sample, the vial including a pipette, a cap assembly, and a container having at least one opening in a body portion of the container to allow liquid and/or gas to enter and/or exit the vial to balance the pressure between the inside of vial and the outside environment. The cryogenic vial allows for reduced processing time and minimizes the chance a sample may be lost or damaged while being processed.

12 Claims, 4 Drawing Sheets

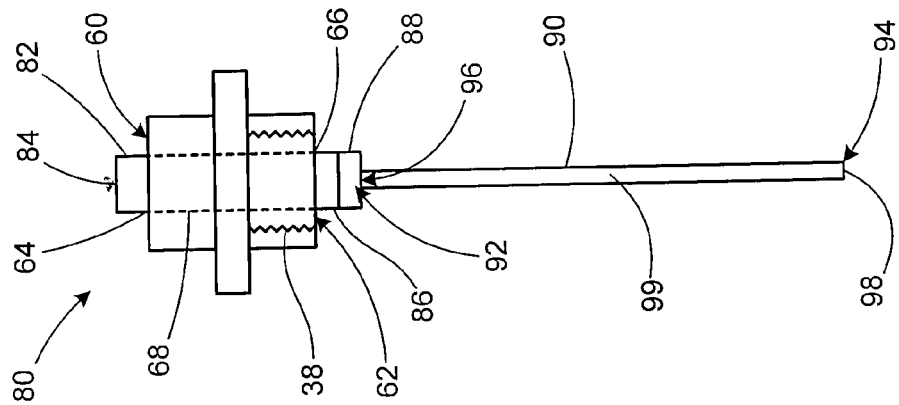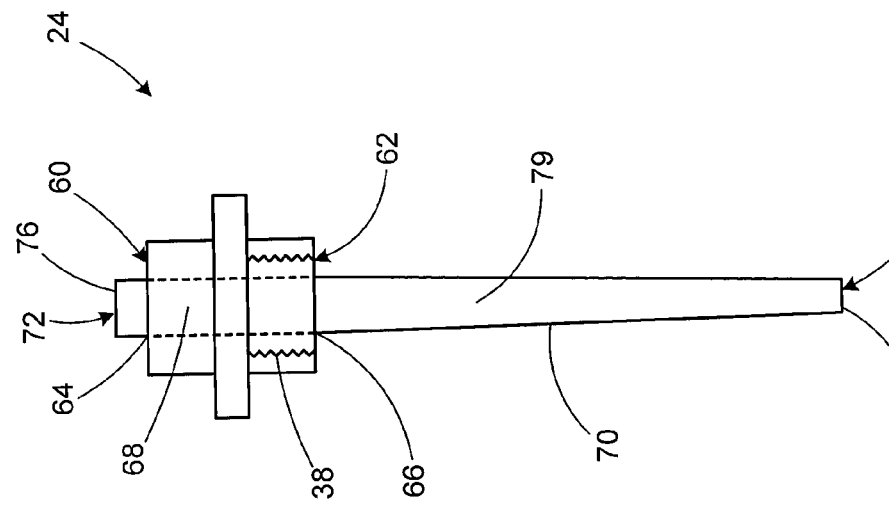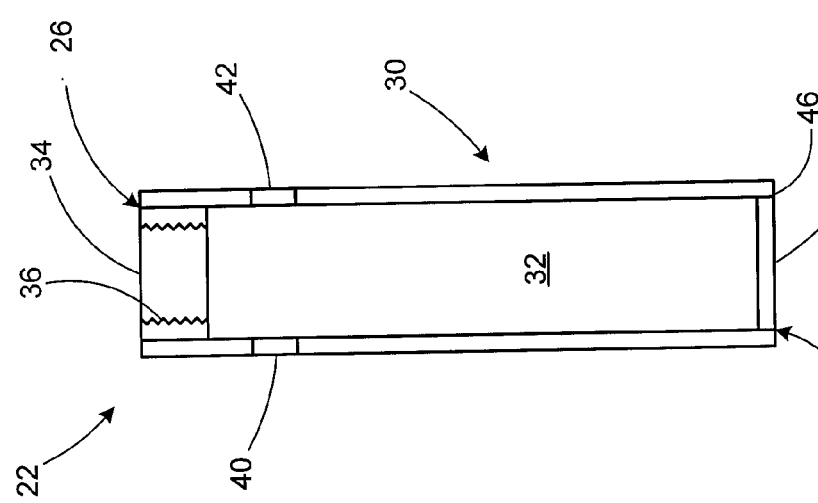

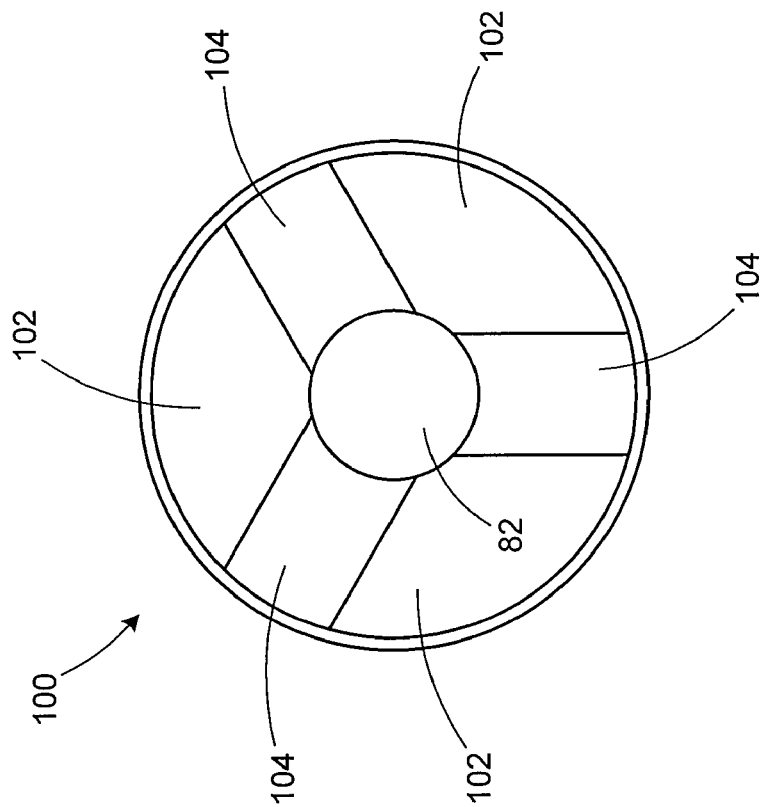
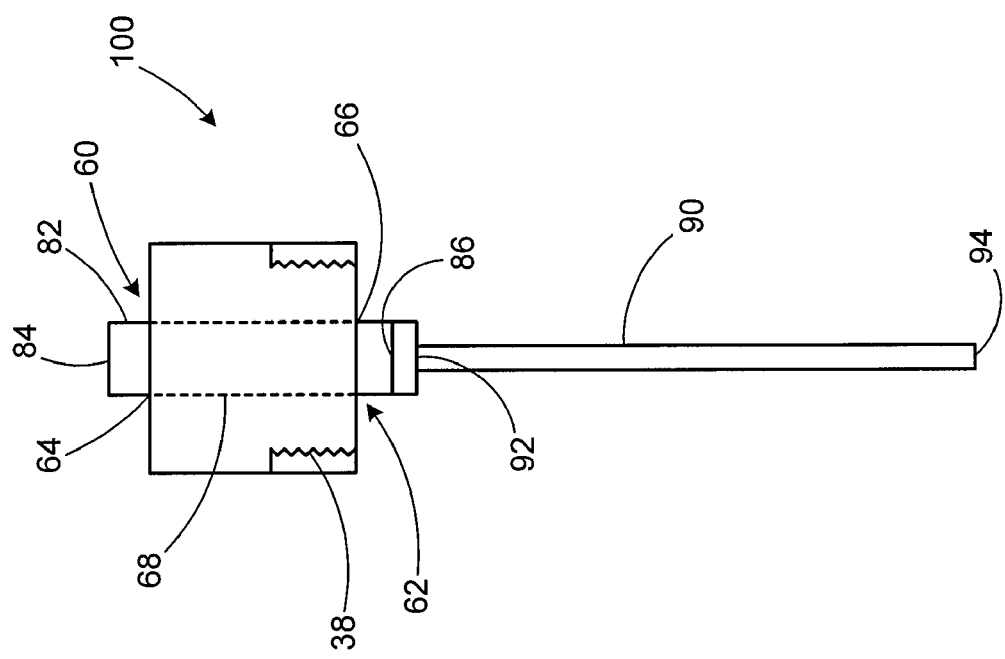

CRYOGENIC VIAL

FIELD OF INVENTION

The present invention relates generally to specimen containers and, more particularly, to cryogenic vials for storing biological specimens.

BACKGROUND

Biological samples may be cryogenically preserved by immersing them in a suitable freezing medium, such as liquid nitrogen. The faster some samples freeze, the less damage is done to the samples. Similarly, when thawing the samples, the faster the samples arrive at a designated temperature, the less damage is done to the samples.

Conventional cryogenic vials, indicated by reference numeral 10 in FIG. 1, consist of a cap 12 that is threaded onto a container 14. The vial 10 may be used to store the biological samples, which may include cells, for example. The samples may be transferred from a dish to the vial 10 by a pipette, for example, and stored in the bottom of the container 14. The vial 10 is suspended in a freezer that is supplied with liquid nitrogen that maintains the freezer at extremely low temperatures to preserve the cells. When the cells are thawed, the samples may be removed from the vial 10 by using a pipette.

SUMMARY OF INVENTION

The present invention provides a cryogenic vial for storing at least one sample, the vial including a pipette, a cap assembly, and a container having at least one opening in a body portion of the container to allow liquid and/or gas to enter and/or exit the vial to balance the pressure between the inside of vial and the outside environment. The cryogenic vial allows for reduced processing time and minimizes the chance a sample may be lost or damaged while being processed. Additionally, because the pipette may be directly submerged in the liquid and/or gas and because the pipette may be very thin, the freezing process is much quicker than with conventional vials.

More particularly, the cryogenic vial includes a pipette configured to receive the sample, the pipette having a top and a bottom portion having respective openings and a passage extending between the openings. The vial also includes a cap assembly having a top and a bottom portion having respective openings and a passage extending between the openings, the cap assembly being coupled to the pipette. Further, the vial includes a container having a top portion, a bottom portion and a body portion, the body portion forming a cavity configured to receive the pipette, wherein the container has an opening at the top portion configured to receive the cap assembly, at least one opening in the body portion configured to allow vapor to enter and exit the container, and an opening in the bottom portion configured to receive a valve.

The pipette may extend through the passage in the cap, and the top portion of the pipette may be configured to be coupled to a transfer device and the bottom portion of the pipette is configured to receive and store the sample. Alternatively, the vial may include a connector disposed in the passage in the cap, wherein a top portion of the connector is configured to be coupled to a sample transfer device and a bottom portion of the connector is coupled to a seal, and wherein the top portion of the pipette is coupled to the seal.

According to a further aspect of the invention, a method for storing a biological sample using a cryogenic vial having a pipette, a container and a cap assembly, the pipette being coupled to the cap assembly and the cap assembly being configured to be coupled to the container includes the steps of coupling a transfer device to a top portion of the cap assembly, drawing the sample in the pipette by creating negative pressure using the transfer device, uncoupling the transfer device from the top portion of the cap assembly, and coupling the cap assembly to the container.

The foregoing and other features of the invention are hereinafter described in greater detail with reference to the accompanying drawings.

BRIEF DESCRIPTION OF THE DRAWINGS

FIG. 3 is a cross-sectional of the container shown in FIG. 2.

FIG. 4 is a cross-sectional of the cap assembly shown in FIG. 2.

FIG. 5 is a cross-sectional of another cap assembly in accordance with the invention.

FIG. 6 is a cross-sectional view of yet another cap assembly in accordance with the invention.

FIG. 7 is a top view of the cap assembly shown in FIG. 6.

DETAILED DESCRIPTION

Figure 2:
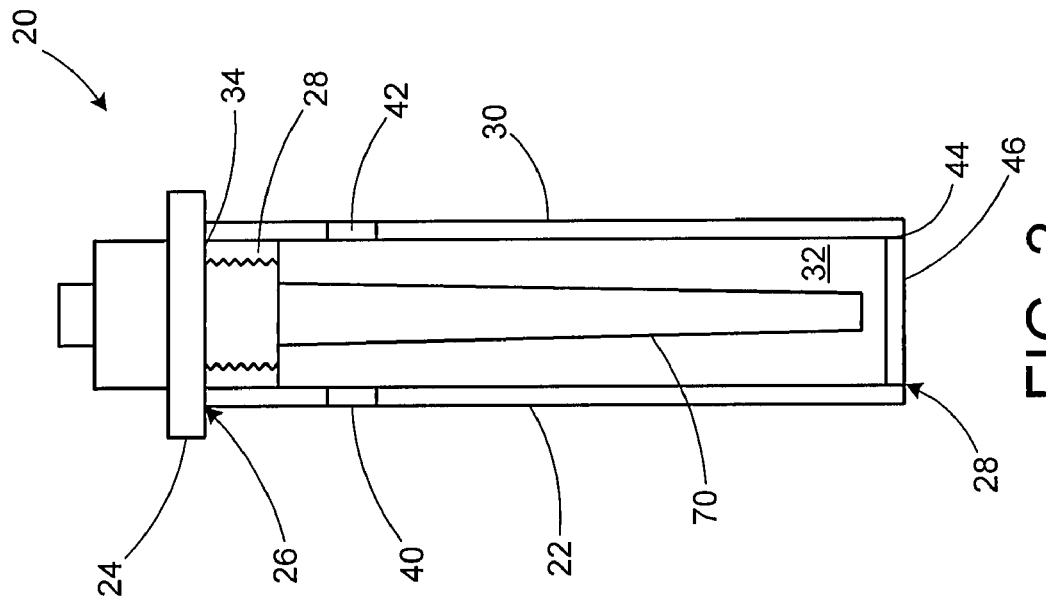
FIG. 2 is a cross-sectional view of a cryogenic vial including a cap assembly and a container in accordance with the invention.
Figure 1:
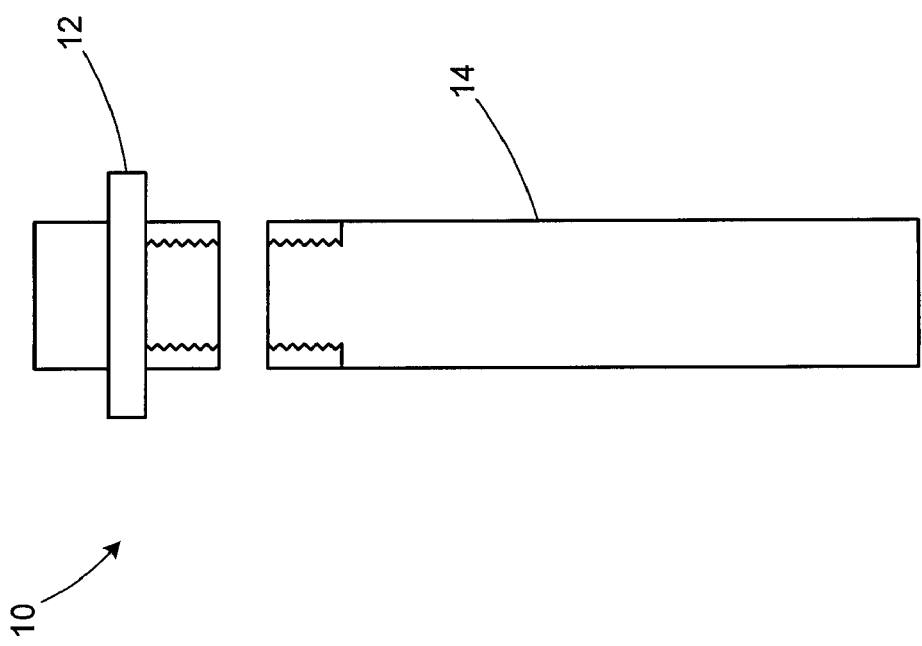
FIG. 1 is a cross-sectional view of a conventional cryogenic vial.

Referring now to the drawings in detail, and initially to FIGS. 2 and 3, an exemplary cryogenic vial 20 is shown. The vial is configured to hold a sample being cryogenically preserved, for example a sample that is to be immersed in a suitable freezing medium, such as liquid nitrogen. The cryogenic vial 20 includes a container 22 and a cap assembly 24 configured to be secured to the container. The container has a top portion 26, a bottom portion 28 and a body portion 30 forming a cavity 32. In the illustrated embodiment the container is tubular in shape, although it will be appreciated that the container can be any other suitable shape, such as a triangular shape.

At the top portion 26 of the container is an opening 34 for receiving the cap assembly 24. In the illustrated embodiment, the container is provided with a threaded portion 36 for receiving a threaded portion 38 of the cap assembly 24 to secure the cap assembly to the container. It will be appreciated, however, that the cap assembly may be secured to the container by other suitable means such as a by a rubber stopper on a bottom portion of the cap assembly.

At the body portion 30 of the container 22 is at least one opening 40, and in the illustrated embodiment, two openings 40 and 42 are provided, although it will be appreciated that any suitable number of openings may be provided at various locations in the body portion 30. The openings 40 and 42 allow the sample to reach a lower and more consistent temperature than conventional vials, thereby allowing the vial to better preserve samples. Additionally, the openings 40 and 42 allow liquid and/or gas to enter and/or exit the container 22, for example when the sample is being thawed. Allowing the liquid and/or gas to exit the container prevents the buildup of vapor, which may cause the vial to explode. Further, allowing liquid and/or gas to enter and/or exit the container allows the pressure between the vial and the outside environment to be balanced, thereby prevention the vial from exploding. Moreover, allowing liquid and/or gas to enter and/or exit the container prevents damage to the sample caused by rapid change in the air pressure.

At the bottom portion of the container is an opening 44 for receiving a valve 46. The valve 46 is configured to blowout when the vial 20 is being thawed if the pressure inside the vial is greater than a predetermined pressure, the predetermined pressure being the highest pressure where no damage will occur to the sample or the vial. The blowout allows the vapor to escape the vial at a greater rate then allowed for by openings 40 and 42 alone. The valve may be made of any suitable material, such as wax, plastic, etc., and may be reusable or disposable.

Turning now to FIG. 4, the exemplary cap assembly 24 is shown. The cap assembly has a top portion 60 and a bottom portion 62. At the top and bottom portions 60 and 62 are openings 64 and 66, respectively, and extending between the openings is a passage 68. In the illustrated embodiment the cap assembly is tubular in shape, although it will be appreciated that the cap assembly can be any other suitable shape, such as a triangular shape. The cap assembly is configured to be coupled to any suitable sample transfer device, such as an aspirator tube or pipette gun, to draw or transfer one or more samples into or out of a tube, such as a pipette 70.

The pipette 70, which is configured to receive and store samples, includes a top portion 72 and a bottom portion 74 having respective openings 76 and 78 and a passage 79 extending between the openings allowing for fluid flow. The pipette may be made of any suitable material such as glass or plastic. Additionally, the pipette may have any suitable diameter, which may be uniform from the top portion 72 of the pipette to the bottom portion 74 of the pipette or which may gradually decrease from the top portion 72 to the bottom portion 74, as shown. Further, the pipette may have a length that is less than the length of the body portion 30 of the container 22, which allows the sample to be suspended in the container 22 and prevents the sample from contacting the bottom of the container.

The pipette 70 is configured to extend through the passage 68 and may be coupled to the cap assembly 24 by any suitable means or may be integrally formed the cap assembly. As shown, the top portion 72 of the pipette is configured to be coupled to the transfer device and the bottom portion 74 is configured to receive and store the sample. Alternatively, the pipette 70 may be coupled the bottom portion 66 of the cap assembly and a separate connector (shown in FIG. 5) may be coupled to the top portion 64 of the cap assembly.

As will now be appreciated, to store a biological sample in the foregoing construction of the cryogenic vial 20, the cap assembly 24 is coupled to a transfer device, such as a pipette gun, and the biological sample is drawn into the bottom portion 74 of the pipette 70 by negative pressure created by the transfer device. The cap assembly 24 is then coupled to the container 22 (which is filled with liquid nitrogen), either before or after uncoupling the transfer device from the cap assembly. In this way, the freezing process is faster than with conventional vials. Additionally, by storing the sample in the pipette, the foregoing construction of the cryogenic vial eliminates the need to transfer the sample from a pipette into a container, thereby reducing the chance of the sample being lost during the transfer process.

When a plurality of cryogenic vials is frozen together, for example in the same storage container, and one or more of the vials is being removed to be thawed, typically all of the vials are removed from the freezer together. Because each vial contains liquid nitrogen, the foregoing construction of the cryogenic vial minimizes the temperature change of the samples in the vials that are to be returned to the freezer. Additionally, when the vials are returned to the freezer, the vials can be refilled by liquid nitrogen entering the vials vial openings 40 and 42.

Turning now to FIG. 5, another embodiment of the cap assembly is shown indicated by reference numeral 80. The cap assembly 80 is substantially the same as the above-referenced cap assembly 24, and consequently the same reference numerals are used to denote structures corresponding to similar structures in the cap assembly 80. In addition, the foregoing description of the cap assembly 24 is equally applicable to the cap assembly 80 except as noted below.

The cap assembly 80 includes a connector 82 which is disposed in the passage 68. The connector is configured to extend beyond the openings 64 and 66, although it will be appreciated that the connector may not extend beyond either or both of openings 64 and 66. The connector includes a top portion 84 configured to couple to the transfer device and a bottom portion 86 configured to couple to a seal 88. The seal may be any suitable seal, such as a silicone seal, and may be coupled to the bottom portion 86 by any suitable means.

The cap assembly 80 also includes a pipette 90 having a top portion 92 and a bottom portion 94. The top portion 92 is configured to couple to the seal 88 by any suitable and the bottom portion 94 is configured to receive and store the sample. The top and bottom portions 92 and 94 have respective openings 96 and 98 and a passage 99 extending between the openings. The pipette may have any suitable diameter, for example, the diameter may be uniform from the top portion 92 to the bottom portion 94 as shown.

Turning now to FIGS. 6 and 7, another embodiment of the cap assembly is shown indicated by reference numeral 100. The cap assembly 100 is substantially the same as the above-referenced cap assembly 80, and consequently the same reference numerals are used to denote structures corresponding to similar structures in the cap assembly 100. In addition, the foregoing description of the cap assembly is equally applicable to the cap assembly 100 except as noted below.

FIG. 6 shows a cross-sectional view of the cap assembly 100, and FIG. 7 shows a top view of the cap assembly. As shown in FIG. 7, the cap assembly includes a plurality of gaps 102 extending from the top portion 60 to the bottom portion 62 that allow nitrogen vapor to enter and/or exit the container. The gaps may be used in combination with, or in place of openings 40 and 42 in the container 22 to provide a flow path for the vapor. The gaps 102 and the cavity 68 are formed by a plurality of supports 104, which extend from the top portion 60 to the bottom portion 62. The supports are coupled to an inner wall of the cap assembly and are configured to support the connector 82. Alternatively, the supports may be configured to support a pipette extending through the cavity, similar to the embodiment shown in FIG. 4.

Figure 9:
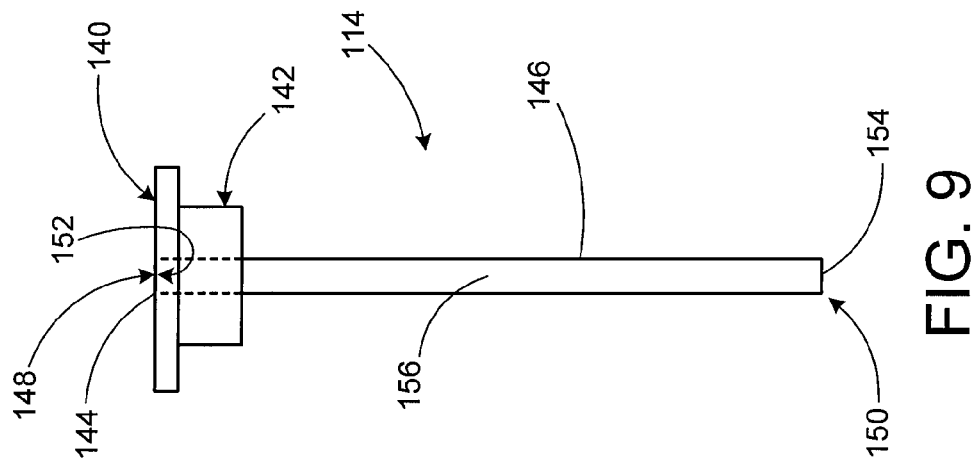
FIG. 9 is a side view of the cap assembly shown in FIG. 8.
Figure 8:
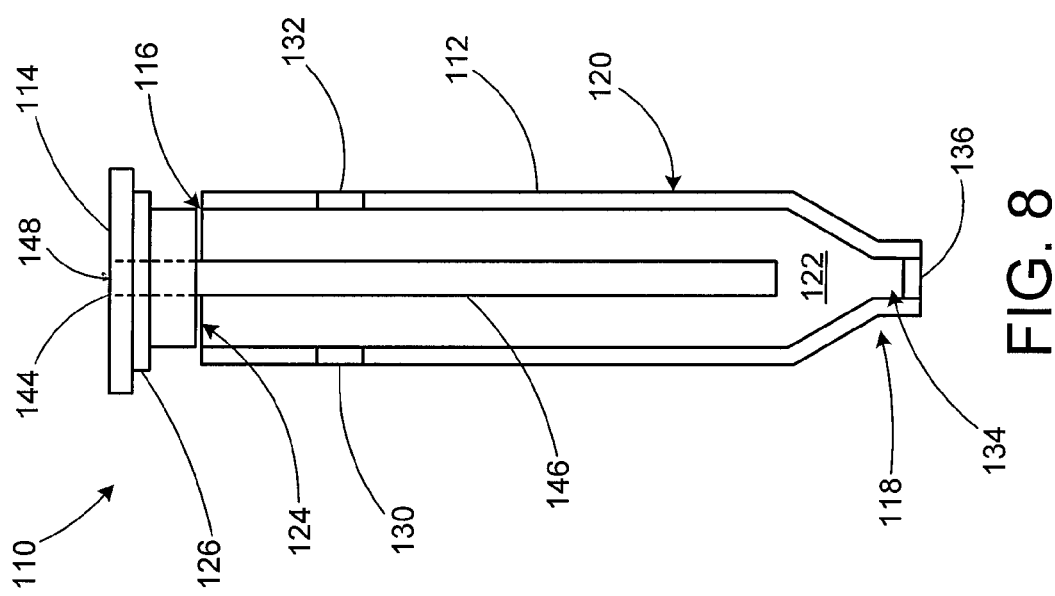
FIG. 8 is a cross-sectional view of another cryogenic vial including a cap assembly and a container in accordance with the invention.

Turning now to FIGS. 8 and 9, another embodiment of a cryogenic vial is shown indicated by reference numeral 110. The cryogenic vial 110 includes a container 112 and a cap assembly 114 configured to be secured to the container. The container has a top portion 116, a bottom portion 118 and a body portion 120 forming a cavity 122. In the illustrated embodiment the container is tubular in shape, although it will be appreciated that the container can be any other suitable shape, such as a triangular shape.

At the top portion of the container is an opening 124 for receiving the cap assembly 114. In the illustrated embodiment, the cap assembly 114 may be coupled to the container 112 by a snap lock mechanism and may be sealed by a suitable seal, such as o-ring 126. At the body portion 120 of the container 112 is at least one opening 130, and in the illustrated embodiment, two openings 130 and 132 are provided, although it will be appreciated that any suitable number of openings may be provided at various locations in the body portion 120. The openings 130 and 132 operate in a similar manner to the openings 40 and 42 discussed above. At the bottom portion of the container is an opening 134 for receiving a valve 136, which is configured to operate in a similar manner to the valve 46 discussed above.

Turning now to FIG. 9, the exemplary cap assembly 114 is shown. The cap assembly has a top portion 140 and a bottom portion 142. At the top portion is an opening 144, which is in fluidic communication with the bottom portion 142, which is hollow. In the illustrated embodiment the cap assembly is tubular in shape, although it will be appreciated that the cap assembly can be any other suitable shape, such as a triangular shape. The cap assembly is configured to be coupled to a pipette 146 at the opening 144, or the pipette may be integrally formed with the cap assembly. A top portion 148 of the pipette is configured to be coupled to the transfer device and a bottom portion 150 of the pipette is configured to receive and store the sample. The top and bottom portions 148 and 150 have respective openings 152 and 154 and a passage 156 extending between the openings. The pipette may be made of any suitable material such as glass or plastic and may have any suitable diameter and length as described above regarding the pipette 70.

Although the invention has been shown and described with respect to a certain embodiment or embodiments, it is obvious that equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

What is claimed is:

1. A cryogenic vial for storing at least one sample, the vial including:
   a pipette configured to receive the sample, the pipette having a top and a bottom portion having respective openings and a passage extending between the openings;
   a cap assembly having a top and a bottom portion having respective openings and a passage extending between the openings, the cap assembly being coupled to the pipette; and
   a container having a top portion, a bottom portion and a body portion, the body portion forming a cavity configured to receive the pipette, wherein the container has an opening at the top portion configured to receive the cap assembly, at least one opening in the body portion configured to allow vapor to enter and exit the container, and an opening in the bottom portion configured to receive a valve.

2. A cryogenic vial according to claim 1, wherein the pipette extends through the passage in the cap.

3. A cryogenic vial according to claim 2, wherein the top portion of the pipette is configured to be coupled to a transfer device and the bottom portion of the pipette is configured to receive and store the sample.

4. A cryogenic vial according to claim 1, further comprising a connector disposed in the passage in the cap, wherein a top portion of the connector is configured to be coupled to a sample transfer device and a bottom portion of the connector is coupled to a seal.

5. A cryogenic vial according to claim 4, wherein the top portion of the pipette is coupled to the seal.

6. A cryogenic vial according to claim 1, further comprising the valve, wherein the valve is coupled to the container at the opening in the bottom portion.

7. A cryogenic vial according to claim 6, wherein the valve is configured to blowout if pressure inside the valve is greater than a predetermined pressure.

8. A cryogenic vial according to claim 1, wherein the cap assembly includes a plurality of gaps extending from the top portion to the bottom portion to allow nitrogen vapor to enter and exit the container.

9. A cryogenic vial according to claim 8, wherein the plurality of gaps are formed by a plurality of supports extending from the top portion to the bottom portion.

10. A cryogenic vial according to claim 1, wherein the cap assembly is coupled to the container by a snap lock mechanism.

11. A cryogenic vial according to claim 10, wherein the cap assembly is sealed to the container by a seal.

12. A cryogenic vial according to claim 1, wherein the container includes a threaded portion configured to receive a threaded portion of the cap assembly to secure the cap assembly to the container.

* * * * *